US011491218B2

United States Patent
Aguilar Rubido et al.

(10) Patent No.: US 11,491,218 B2
(45) Date of Patent: Nov. 8, 2022

(54) PHARMACEUTICAL COMPOSITION THAT INCLUDES THE SURFACE AND NUCLEOCAPSID ANTIGENS OF THE HEPATITIS B VIRUS

(71) Applicant: CENTRO DE INGENIERÍA GENÉTICA Y BIOTECNOLOGÍA, Havana (CU)

(72) Inventors: Julio César Aguilar Rubido, Havana (CU); Yadira Lobaina Mato, Havana (CU); Enrique Iglesias Perez, Havana (CU); Eduardo Pentón Arias, Havana (CU); Gerardo Enrique Guillén Nieto, Havana (CU); Jorge Agustín Aguiar Santiago, Havana (CU); Sonia Gonzalez Blanco, Havana (CU); Jorge Valdes Hernandez, Havana (CU); Mariela Vazquez Castillo, Havana (CU)

(73) Assignee: CENTRO DE INGENIERÍA GENÉTICA Y BIOTECNOLOGÍA, Havana (CU)

( * ) Notice: Subject to any disclaimer, the term of this patent is extended or adjusted under 35 U.S.C. 154(b) by 261 days.

(21) Appl. No.: 16/088,188

(22) PCT Filed: Mar. 14, 2017

(86) PCT No.: PCT/CU2017/050001
§ 371 (c)(1),
(2) Date: Sep. 25, 2018

(87) PCT Pub. No.: WO2017/167317
PCT Pub. Date: Oct. 5, 2017

(65) Prior Publication Data
US 2020/0297840 A1    Sep. 24, 2020

(30) Foreign Application Priority Data

Mar. 31, 2016 (CU) .................................. 2016-0038

(51) Int. Cl.
| | | |
|---|---|---|
| A61K 39/39 | (2006.01) | |
| A61P 31/20 | (2006.01) | |
| A61K 39/29 | (2006.01) | |
| A61K 39/00 | (2006.01) | |

(52) U.S. Cl.
CPC ............ *A61K 39/292* (2013.01); *A61K 39/39* (2013.01); *A61P 31/20* (2018.01); *A61K 2039/5258* (2013.01); *A61K 2039/543* (2013.01); *A61K 2039/555* (2013.01); *A61K 2039/575* (2013.01)

(58) Field of Classification Search
None
See application file for complete search history.

(56) References Cited

FOREIGN PATENT DOCUMENTS

| EP | 0480525 B1 | 1/1999 |
| EP | 1346727 B1 | 4/2010 |
| EP | 2484343 A1 | 8/2012 |

OTHER PUBLICATIONS

Akbar et al., HBsAg, HBcAg, and combined HBsAg/HBcAgbased therapeutic vaccines in treating chronic hepatitis B virus infection, 2013, Hepatobiliary Pancreat Dis Int, 2013, vol. 12, pp. 363-369).*
Al-Mahtab et al., Therapeutic potential of a combined hepatitis B virus surface and core antigen vaccine in patients with chronic hepatitis B, 2013, Hepatology International, vol. 7, p. 981-989.*
Sominskaya et al., A VLP Library of C-Terminally Truncated Hepatitis B Core Proteins: Correlation of RNA Encapsidation with a Th1/Th2 Switch in the Immune Responses of Mice, 2013, PLoS ONE, vol. 8, No. 9.*
Hernandez-Bernal et al., Comparison of four recombinant hepatitis B vaccines applied on an accelerated schedule in healthy adults, Human Vaccines, 2011, vol. 7, No. 10, pp. 1026-1036.*
Tey, Beng Ti, et al. "Optimal Conditions for Hepatitis B Core Antigen Production in Shaked Flask Fermentation." Biotechnology and Bioprocess Engineering 9.5 (2004): 374-378.
Palenzuela, Daniel O, et al. "Purification of the Recombinant Hepatitis B Core Antigen, and its Potential Use for the Diagnosis of Hepatitis B Virus Infection." Biotecnología Aplicada 19.3 (2002): 138-142.
Lobaina, Yadira, et al. "Comparison of the Immune Response Induced in Mice by Five Commercial Vaccines Based on Recombinant HBsAg from Different Sources, Implications on Their Therapeutic Use." Biotecnología Aplicada 25.4 (2008): 325-331.
Aguilar, J. C., et al. "Development of a Nasal Vaccine for Chronic Hepatitis B Infection that uses the Ability of Hepatitis B Core Antigen to Stimulate a Strong Th1 Response Against Hepatitis B Surface Antigen." Immunology and Cell Biology 82.5 (2004): 539-546.
Betancourt, Arístides Aguilar, et al. "Phase I Clinical Trial in Healthy Adults of a Nasal Vaccine Candidate Containing Recombinant Hepatitis B Surface and Core Antigens." International Journal of Infectious Diseases 11.5 (2007): 394-401.

(Continued)

*Primary Examiner* — Benjamin P Blumel
(74) *Attorney, Agent, or Firm* — Hoffmann and Baron LLP (57) ABSTRACT

This invention reveals the pharmaceutical composition that includes the surface antigen (HBsAg) of the hepatitis B virus (HBV) and the antigen of the nucleocapsid (or core, HBcAg) of the same virus. The HBcAg of this composition contains messenger ribonucleic acid (mRNA) at a proportion of over 45% of the total amount of ribonucleic acid (RNA) in this antigen. Because of the changes in the constitution of the antigens forming it, the composition of the invention is useful for the prevention or treatment of chronic hepatitis B. It also covers the use of this pharmaceutical composition in the production of a drug for immuno-prophylaxis or immunotherapy against HBV infection, and its use to increase the immune response against an additional antigen that is co-administered with the mixture of these antigens.

4 Claims, 1 Drawing Sheet

(56) References Cited

OTHER PUBLICATIONS

Riedl, Petra, et al. "Priming Th1 Immunity to Viral Core Particles is Facilitated by Trace Amounts of RNA Bound to its Arginine-Rich Domain." The Journal of Immunology 168.10 (2002): 4951-4959.
Scheel, Birgit, et al. "Immunostimulating Capacities of Stabilized RNA Molecules." European Journal of Immunology 34.2 (2004): 537-547.
Aguilar, J. C. "Efecto Adyuvante de los Antígenos de la Superficie y la Nucleocápsida del Virus de la Hepatitis B y su Utilidad en el Desarrollo de Candidatos Vacunales." División de Vacunas (2007).
Hilleman, Maurice R. "Overview of the Pathogenesis, Prophylaxis and Therapeusis of Viral Hepatitis B, with Focus on Reduction to Practical Applications." Vaccine 19.15-16 (2001): 1837-1848.
Nash, Kathryn. "Telbivudine in the Treatment of Chronic Hepatitis B." Advances in Therapy 26.2 (2009): 155-169.
Yang, Ninghan, et al. "Advances in Therapeutics for Chronic Hepatitis B." Hepatology International 10.2 (2016): 277-285.
Yalcin, K., et al. "Specific Hepatitis B Vaccine Therapy in Inactive HBsAg Carriers: a Randomized Controlled Trial." Infection 31.4 (2003): 221-225.
Zuckerman, Jane N., et al. "Immune Response to a New Hepatitis B Vaccine in Healthcare Workers Who had not Responded to Standard Vaccine: Randomised Double Blind Dose-Response Study." BMJ 314.7077 (1997): 329.
Bertoletti, Antonio, et al. "Therapeutic Vaccination and Novel Strategies to Treat Chronic HBV Infection." Expert Review of Gastroenterology & Hepatology 3.5 (2009): 561-569.
Penna, A., et al. "Hepatitis B Virus (HBV)-Specific Cytotoxic T-Cell (CTL) Response in Humans: Characterization of HLA Class II-Restricted CTLs that Recognize Endogenously Synthesized HBV Envelope Antigens." Journal of Virology 66.2 (1992): 1193-1198.
Ferrari, C., et al. "Identification of Immunodominant T Cell Epitopes of the Hepatitis B Virus Nucleocapsid Antigen." The Journal of Clinical Investigation 88.1 (1991): 214-222.
Tsai, S. L., et al. "Acute Exacerbations of Chronic Type B Hepatitis are Accompanied by Increased T Cell Responses to Hepatitis B Core and e Antigens. Implications for Hepatitis B e Antigen Seroconversion." The Journal of Clinical Investigation 89.1 (1992): 87-96.
Lobaina, Yadira, et al. "In Vitro Stimulation with HBV Therapeutic Vaccine Candidate Nasvac Activates B and T Cells from Chronic Hepatitis B Patients and Healthy Donors." Molecular Immunology 63.2 (2015): 320-327.
Dikici, Bunyamin, et al. "Failure of Therapeutic Vaccination Using Hepatitis B Surface Antigen Vaccine in the Immunotolerant Phase of Children with Chronic Hepatitis B Infection." Journal of Gastroenterology and Hepatology 18.2 (2003): 218-222.
Garcia-Diaz, Darien, et al. "Th2-Th1 Shift with the Multiantigenic Formulation TERAVAC-HIV-1 in Balb/c Mice." Immunology Letters 149.1-2 (2013): 77-84.

Iglesias, E., et al. "Chimeric Proteins Containing HIV-1 T Cell Epitopes: Expression in E. coli, Purification and Induction of Antibodies in Mice." J Biochem Mol Biol Biophys 5 (2001): 109-20.
Pol, Stanislas, et al. "Efficacy and Limitations of a Specific Immunotherapy in Chronic Hepatitis B." Journal of Hepatology 34.6 (2001): 917-921.
Page, M., et al. "A Novel, Recombinant Triple Antigen Hepatitis B Vaccine (Hepacare®)." Intervirology 44.2-3 (2001): 88-97.
Yap, I., et al. "A New Pre-S Containing Recombinant Hepatitis B Vaccine and Its Effect on Non-Responders: A Preliminary Observation." Annals of the Academy of Medicine, Singapore 25.1 (1996): 120-122.
Medeva PLC, "Results from Immunotherapy Trial in Asian Patients" Investegate, Jan. 17, 2000, https://www.investegate.co.uk/article.aspx?id=200001171532169093D, accessed Nov. 4, 2019.
Dahmen, Anja, et al. "Clinical and Immunological Efficacy of Intradermal Vaccine Plus Lamivudine With or Without Interleukin-2 in Patients With Chronic Hepatitis B." Journal of Medical Virology 66.4 (2002): 452-460.
Horiike, Norio, et al. "In Vivo Immunization by Vaccine Therapy Following Virus Suppression by Lamivudine: A Novel Approach for Treating Patients With Chronic Hepatitis B." Journal of Clinical Virology 32.2 (2005): 156-161.
Ul-Haq, Najib, et al. "Immunogenicity of 10 and 20 μg Hepatitis B Vaccine in a Two-Dose Schedule." Vaccine 21 (2003): 3179-3185.
Vandepapeliere, Pierre, et al. "Therapeutic Vaccination of Chronic Hepatitis B Patients With Virus Suppression by Antiviral Therapy: A Randomized, Controlled Study of Co-Administration of HBsAg/AS02 Candidate Vaccine and Lamivudine." Vaccine 25.51 (2007): 8585-8597.
Pol, Stanislas, et al. "Vaccination Against Hepatitis-B Virus—An Efficient Immunotherapy Against Hepatitis-B Multiplication." Comptes Rendus de L Academie des Sciences Serie III—Sciences de la Vie—Life Sciences 316.7 (1993): 688-691.
Marinos, George, et al. "Induction of T-Helper Cell Response to Hepatitis B Core Antigen in Chronic Hepatitis B: A Major Factor in Activation of the Host Immune Response to the Hepatitis B Virus." Hepatology 22.4 (1995): 1040-1049.
Jones, Christopher D., et al. "T-Cell and Antibody Response Characterisation of a New Recombinant Pre-S1, Pre-S2 and SHBs Antigen-Containing Hepatitis B Vaccine; Demonstration of Superior Anti-SHBs Antibody Induction in Responder Mice." Vaccine 17.20-21 (1999): 2528-2537.
Nagaraju, K., et al. "Functional Implications of Hepatitis B Surface Antigen (HBsAg) in the T Cells of Chronic HBV Carriers." Journal of Viral Hepatitis 4.4 (1997): 221-230.
Gonzalez, Verena Muzio, et al., "Post-Licensing Studies of the Cuban Hepatitis B Vaccine, Heberbiovac-HB", Biotecnologia Aplicada, vol. 18, No. 2 (2001): 103-104.

\* cited by examiner

PHARMACEUTICAL COMPOSITION THAT INCLUDES THE SURFACE AND NUCLEOCAPSID ANTIGENS OF THE HEPATITIS B VIRUS

FIELD OF THE INVENTION

This invention is related to the field of medicine, particularly the branch of vaccinology, and specifically to the development of vaccine compositions with increased effectiveness. These compositions include the antigens of the hepatitis B virus (HBV) that has modifications in its chemical composition, which unexpectedly increased their immunogenicity. The HBV antigens that were modified in their chemical composition were the surface antigen (HBsAg) and the core antigen (HBcAg).

STATE OF THE PREVIOUS TECHNIQUE

The World Health Organization (WHO) considers that nearly half of the world population has been infected by HBV, based on the presence of serological markers of infection. It has been estimated that approximately 5 to 10% of the adults, and up to 90% of the neonates infected by HBV develop chronic hepatitis B (CHB). At present, 350 million persons have persistent or chronic infections. The sustained replication of the virus, for a long period of time, leads to a liver inflammatory process, which leads to the death of 25% of the infected population as a consequence of cirrhosis, hepatocellular carcinoma, or due to other complications such as ascites, esophageal bleeding and splenomegaly. In spite of the universal vaccination of neonates and children in recent years, and of the subsequent reduction of the incidence of new HBV infections, CHB is still a significant health problem at a worldwide scale [Hilleman, M. R. Vaccine (2001), 19, 1837-48].

The treatment with alpha interferon (IFN-α), its pegilated variant (PegIFN) and the nucleotide and nucleoside analogues, such as Tenofovir, Entecavir, Lamivudin, Adefovir-dipivoxil and Telbivudin, are the state of the art of the CHB treatments. In general, these drugs have poor efficacy in relation to the sustained elimination of the HBV after the treatment, and their use is associated to important adverse events (AE), which is widely recognized [Nash K. Adv Ther (2009), 26:155-169; Yang N, Hepatol Int. 2015 Sep. 12. [Epub ahead of print] PubMed PMID: 26363922].

The use of vaccine formulations, as the immunotherapeutic strategy, in the CHB treatment, is an interesting approach. Viral persistence has been associated to a defect in the development of anti-HBV cellular immunity. Since the start of the 1980's, vaccine strategies have been focused on increasing and potentiating the weak response of T cells of CHB patients. These immunotherapeutic strategies initially used commercial anti-HBV vaccines with the aim of introducing specific CD4+ and CD8+ responses against HBV, as well as pro-inflammatory cytokines to control viral replication. Hence, almost all commercial preventive vaccines were tested alone, or together with conventional anti-viral therapies. In previous studies of therapeutic vaccination, the vaccines were administered with or without other anti-viral treatments. Furthermore, immunotherapy with commercial vaccines also proposed schedules with larger amounts of inoculations and alternative parenteral routes were explored. The main studies are summarized below.

A pilot vaccination study in CHB patients using Genhevac B° (Aventis Pasteur, France, produced in —CHO mammal cells) showed a reduction in HBV replication in about 50% of the chronic carriers [Pol S, et al. C R Acad Sci III (1993), 316:688-91]. Another placebo controlled multi-center study, also evaluated the Genhevac B® vaccine, and the Recombivax® (Merck Sharp Dohme-Chibret, France) yeast produced vaccine. A significant difference was observed here at the sixth month (3%, 20% and 22%) among the groups inoculated with Genhevac® and Recombivax®, respectively. The difference, however, disappeared on month 12 [Pol S, J Hepatol (2001); 34:917-21]. It was concluded that no clear benefit was observed, and the pre-S2 antigen found in the Genhevac® did not seem to have any additional effect.

Other studies where the therapeutic Genhevac® vaccine was evaluated [Yalcin K, et al. Infection (2003), 31: 221-225; Dikici B, et al. J Gastroenterol Hepatol (2003), 18(2): 218-22] only showed slight benefits associated to the treatment.

The Hepagene® (Medeva Ltd., UK) CHO produced vaccine, includes the three variants of HBsAg (L, S and M), and their results in healthy volunteers and non-responders demonstrated high levels of immunogenicity [Page M, et al. Intervirology (2001), 44:88-97; Yap I, et al. Ann Acad Med Singapore (1996), 25: 120-122; Zuckerman J N, et al. BMJ (1997), 314: 329; Jones C D, et al. Vaccine (1999), 17(20-21): 2528-37]. Taking this into consideration, a study was carried out to evaluate its therapeutic potential. Eight dosages of 20 µg of the vaccine were administered in two cycles of 4 inoculations, with a 5 month interval between them [Carman W F, et al. J Hepatol (2001); 34:917-921]. At the end of the schedule, 8 out of the 22 patients that completed the schedule had a sustained clearance of the HBV, and 7 patients eliminated the HBeAg. This uncontrolled limited test was followed by a controlled test with a larger number of patients. In this second clinical trial with 103 chronic patients that were HBeAg positive, four doses of the vaccine or of the placebo were administered at intervals of one and 8 months, and afterwards, all subjects received 8 additional dosages at one-month intervals. At the end of the treatment, no significant clinical benefits were obtained [Medeva PLC. http://www.investegate.co.uk/article.aspx?id=2000011715321690 93D (consulted Oct. 20, 2015)].

In order to favor the development of an anti-viral immune response, treatments have combined the therapeutic vaccination with conventional anti-viral therapies. This strategy takes into consideration the finding related to the effect of the lamivudine, which increases the frequency of the specific T-HBV cells in the peripheral blood, as a result of the inhibition of viral replication [Bertoletti A et al. Expert Rev Gastroenterol Hepatol (2009), 3(5): 561-9].

The combined anti-viral vaccination strategy should favor a greater reactiveness of the T cell response for HBV, but it can also be considered to be safer, since it should avoid liver damage, as a consequence of the activation of the immune system. However, there is no evidence showing that the activation of the specific immune response by the vaccine in CHB patients can produce fulminant hepatitis.

A study published in 2002 assessed the intra-dermal administration (ID) of the Engerix B® (GlaxoSmithKline) vaccine with lamivudine [Dahmen A, et al. J Med Virol 2002; 66:452-60], in patients with CHB. Six dosages of Engerix B®, once a month, combined with the daily administration of lamivudine were used. An additional group received the same treatment together with the sub-cutaneous (SC) daily administration of interleukin 2 (IL-2). After completing the therapy, 7 out of 9 patients from the first group and 2 out of 5 patients from the second group, had reduced their viral load to undetectable levels. Four responders eliminated the virus and normalized the transaminases. In another clinical trial, the combination of therapeutic vaccination through the ID route was evaluated, using a vaccine containing HBsAg in alum, with the daily administration of lamivudine for one year [Horiike N, et al. J Clin Virol (2005), 32: 156-161]. These studies showed that the combined therapy is effective and with little complications for CHB patients. However, in both cases the ID route was used and this could favor the immunogenicity of the vaccine.

The same surface antigen, formulated in a potent adjuvant was not effective in a combined therapy with lamivudine, thus suggesting that the effect of the immunization route should not be ignored, and that this is possibly a crucial element for the future of vaccination.

The study closing the long clinical evaluation period of the vaccine candidates for the viral load suppression conditions is the report of Vandepapeliere et al. [Vandepapeliere P, et al. Vaccine (2007) December 12; 25(51):8585-97]. This was a study on the clinical evaluation of a vaccine candidate based on a formulation of adsorbed HBsAg, injected through the intra-muscular (IM) route in 100 μg of HBsAg together with an oily adjuvant and with potent immune-modulators, such as lipid monophosphoryl A and saponin QS21. Ten administrations under reduced viral load conditions showed no advantages in relation to virological response, when compared to the control group that was treated with the anti-viral agent alone.

The amount of knowledge on the characteristics of the immune response of the host, and that on the therapeutic use of conventional vaccines, suggest that the strategies targeted towards the induction of a strong and sustained reactivity of the T cells against antigens of HBV are feasible and represent a hope for the satisfactory treatment of CHB patients.

The absence of immune stimulation against nucleocapsid antigens is probably a main immunological marker of the failure of the therapeutic vaccination based on HBsAg. In fact, the aim of therapeutic vaccination in CHB is to trigger the same natural immune mechanisms that prevail during the acute hepatitis B and that are self-controlled, or in the CHB that goes through seroconversion. If an immunotherapy fails to stimulate these immune responses, it will probably fail to induce seroconversion.

The improvement of the formulations, in terms of antigenic selection and vaccination strategy could be a way of surpassing these difficulties. The characteristics of the proteins of the envelope justify its inclusion in a therapeutic vaccine. Actually, the proteins of the envelope contain numerous epitopes of cells B and T [Penna A, et al. J Virol (1992), 66(2):1193-6; Nayersina R, et al. J Immunol (1993), 150:4659-71], and it is estimated that the antibodies anti-envelope play a critical role in viral suppression, by removing the free viral particles from circulation and preventing the re-infection of susceptible cells. On the other hand, high levels of HBsAg circulate in the serum of CHB patients; this fact could play a main role in maintaining immune tolerance, by the exhaustion of T cells and the suppression of the production of anti-HBs antibodies [Nagaraju K, et al. J Viral Hepat (1997), 4:221-30].

In this sense, it has been suggested that HBcAg is the main antigenic candidate that should be included in a therapeutic vaccine for CHB. During acute self-resolving hepatitis, the epitopic response of T cells is strongly favored and is predominant during the seroconversion in spontaneous or treatment induced CHB [Ferrari C, et al. J Clin Invest (1991), 88:214-22; Marinos G, et al. Hepatology (1995), 22:1040-9; Tsai S L, et al. Clin Invest (1992), 89:87-96].

Up to now, no anti-hepatitis B commercial vaccine has demonstrated enough clinical results that would allow it to compete with the current treatment, or that would simply endorse its introduction in medical practice. However, these vaccines have created great expectations in the treatment field, not only in anti-hepatitis B immunotherapy settings, but in those of other diseases as the infection of the human immunodeficiency virus (HIV) and cancer, among other chronic diseases, either contractible or not. Hence, this strategy demands that there be clinical assessment of new vaccine concepts and the optimization of all related factors. In this sense, a therapeutic vaccine candidate including HBcAg, besides HBsAg, is the result of the development of these immunotherapy strategies.

The Center for Genetic Engineering and Biotechnology (CIGB) produces HBsAg, as a recombinant protein, obtained in the host yeast Pichia pastoris. This antigen has been included in the preventive vaccine Heberbiovac HB® since the beginning of the 1990's [Muzio V, et al. Biotecnología Aplicada (2001) 18; 103-104; ul-Hag N, et al. Vaccine (2003) 21:3179-85].

Additionally, CIGB developed a formulation where the immune response against hepatitis B is extended; this formulation includes HBsAg and HBcAg, as the main components; the antigens are administered through the mucosal route to generate systemic and mucosal response [European Patent No. EP 1136077]. In another patent document of this same center, the generation of aggregated antigenic structures forming particles, are described. This document reveals that the aggregation, delipidation or oxidation, as well as the selection of particles of 30-500 nm, and the formulation of these aggregates, conveniently adjuvanted, favor the immunogenicity of the resulting antigenic preparation [European Patent No. EP1346727]. Combining the strategies stated in both patent documents, CIGB developed the therapeutic vaccine candidate called NASVAC [Lobaina Y, et al. Mol Immunol (2015), 63:320-327], which is administered through the combination of immunization routes. The clinical results of the vaccine formulation are very attractive; however, the effectiveness of the product should be increased with the use of more potent immunogens.

The vaccine strategies that include the main HBV antigens, such as HBsAg and HBcAg, have produced formulations having certain anti-viral effectiveness. However, its improvement is required to increase the number of patients with sustained antiviral response, as well as the number of patients reaching seroconversion of HBsAg to anti-HBsAg.

EXPLANATION OF THE INVENTION

The invention helps solve the above mentioned problem by providing a pharmaceutical composition that is characterized by: 1) the HBcAg antigen that includes the messenger ribonucleic acid (mRNA) at a proportion of more than 45% of the total ribonucleic acid (RNA) of this antigen and 2) the HBsAg antigen of the HBV. In a realization of the invention, the pharmaceutical composition contains HBsAg that includes phosphatidylserine at a proportion of more than 5% of the total lipids forming this antigen.

The inclusion of the HBsAg and HBcAg antigens that have been modified in their chemical constitution in this particular manner, favors the immunological and antiviral properties of this composition for the immunotherapy. However, the above mentioned modifications do not affect the protein composition of the HBsAg and HBcAg antigens of the invention, since their primary, secondary and tertiary structures remain identical, compared to their unmodified variants. Nonetheless, these modifications lead to unexpected characteristics of these antigens, resulting in more potent immunogens. Also, the combination of these modified antigens lead to a formulation with higher therapeutic antiviral effectiveness for CHB treatment.

In the invention the HBcAg was obtained with mRNA at a level of over 45%. In a particular case, this modified antigen was obtained because of the combination of changes in parameters of its fermentation process. In that case, the use of a chemically defined medium and the low rate of specific growth, gave way to a variant of the HBcAg where the proportion of mRNA increased, in comparison with the rest of the RNA present in it.

Although the high immunogenicity of the HBcAg obtained in Escherichia coli has been described, as well as the participation of a component of nucleic acids in the immunogenicity of the complete particulated antigens (of 183 amino acids), up to the present invention the relative effect of each RNA variant was unknown in relation to their specific contribution to the final immunogenicity of the HBcAg. It was surprising to find that the HBcAg with a level of mRNA surpassing 45% was more immunogenic, and developed a stronger Th1 response, compared to the unmodified HBcAg.

The changes in the proportion of the mRNA detected, did not affect the content of total RNA present in the particle, in relation to the protein content. Unexpectedly, it was found that HBcAg containing more than 45% mRNA within the total RNA, had a higher immunogenicity compared to the HBcAg obtained without any modification in its mRNA content. This increase in the immunogenicity included a significant increase in the Th1 cytokines, and an enhanced capacity for the elimination of circulating HBsAg after immunizing CHB transgenic mice and patients.

On the other hand, in this invention we evaluated the HBsAg that contains phosphatidylserine at a level of over 5% of the total amount of phospholipids present in this lipoprotein antigen. Particularly, the increase in the proportion of phosphatidylserine at over 5% of the total amount of phospholipids was demonstrated in relation to the variation of the parameters, such as the increase in the calcium and magnesium concentrations in the fermentation medium, the low specific growth rate and the low pH. However, the invention was not restricted to the HBsAg obtained under these conditions. The increase in the proportion of phosphatidylserine at over 5% was correlated to the increase of the immunogenicity of the resulting antigen, on comparing it to the HBsAg with a lower content of this phospholipid. A significant increase of Th1 cytokines was observed, as well as a greater capacity of eliminating the circulating HBsAg after the immunization of the HBsAg transgenic mice and CHB patients with the HBsAg containing over 5% phosphatidylserine, in relation to the total % of phospholipids.

In the present invention, the particularly modified HBsAg and HBcAg antigens have been selected on the basis of a higher intensity of the immune and antiviral response, compared to the formulations in which the unmodified antigens were used. Furthermore, the formulation containing both antigens was able to produce the seroconversion of the HBsAg to anti-HBsAg in a greater number of individuals, when comparing them to the antigens administered separately, demonstrating the importance and functionality of the modifications detected in the antigens forming part of the composition of this inventions, as well as the superiority of the combined formulations, compared to the individual antigens.

This invention represents a new solution to the problem prevailing in the state of the art on the need for new formulations that would make it possible to potentiate the immune response anti-HBsAg and anti-HBcAg, to achieve more effective treatments for the control of the chronic infection due to HBV. The issue of this invention cannot be considered to be obvious, or derived from the state of the art by knowledgeable persons, since it is the result of the identification of new characteristics of the described antigens. Although these modified antigens maintain their protein composition intact, they are different in relation to the chemical composition of the molecules associated to them.

To the effect of the invention, modified HBcAg is a preparation from the HBcAg that includes mRNA at a proportion of over 45% of the total RNA of that antigen. At the same time, modified HBsAg is the preparation of HBsAg that contains phosphatidylserine at a proportion of over 5% of the total amount of phospholipids of this antigen.

In a realization of the invention the composition having the HBcAg antigen, with the mRNA at a proportion of over 45% of the total RNA of this antigen and the HBsAg antigen of HBV, is characterized because it is formulated for the administration by the parenteral and mucosal routes. To administer the composition of the invention by the mucosal route, and particularly by the nasal route, devices that have been developed and or commercialized for the administration of pharmaceutical formulations through that route may be used.

In a particular realization, this composition is additionally characterized by having a vaccine adjuvant. Within the vaccine adjuvants that may be present in the composition of the invention, for example, we find those that are well known by persons knowledgeable in this technical field, such as aluminum salts, the emulsions of water in oil, developed for human use, stimulators of the immune system, etc. Furthermore, the invention provides the use of the HBcAg antigen that includes the mRNA at a proportion of over 45% of the total RNA of this antigen and the HBsAg antigen for manufacturing a drug for the immunoprophylaxis or immunotherapy against the HBV infection. In a realization of the invention, the HBsAg forming part of this drug has phosphatidylserine at a proportion of over 5% of the total phospholipids of this antigen. In a particular realization, this drug is formulated for administration by the parenteral and mucosal routes. In a preferred realization the drug with HBcAg, having mRNA at a proportion of over 45% of the total RNA of this antigen, and the HBsAg antigen, is used in the treatment of CHB patients or patients with co-infections, where one of the infecting viruses is HBV. Additionally, on treating the CHB patients with this drug, the use leads to the prevention of hepatocellular cancer derived from HBV infection.

When the drug having HBcAg with mRNA at a proportion of over 45% of the total RNA of this antigen and the HBsAg antigen is used in the treatment of CHB patients by immunotherapy, this can be done in an active manner (through immunization of the patients with this drug) or in a passive form, through cellular stimulation. Because of its components, the pharmaceutical formulation of the invention can be used in the stimulation of autologous or heterologous cells. Hence, the invention results in a cellular stimulation method with this formulation, and the later passive immunization of the patients with CHB, based on the maximum stimulation, in vivo or in vitro, of autologous or heterolgouse cells that include dendritic cells, B cells and macrophages.

Furthermore, the current invention reveals a method for immunoprophylaxis, or the immunotherapy against the HBV infection that is characterized because it administers to an individual needing it, an effective amount of a pharmaceutical composition comprising the HBcAg antigen that has mRNA at a proportion of over 45% of the total RNA of this antigen and the HBsAg antigen of the HBV. In a realization of the invention, the HBsAg comprises phosphatidylserine at a proportion of over 5% of the total amount of phospholipids of this antigen. In a materizlization of the invention, this pharmaceutical composition is administered by the parenteral and mucosal routes. In a preferred realization, the individual receiving the immunotherapy is a patient with CHB. In this case, the application of the invention method for the immunotherapy of the CHB patients produces the prevention of hepatocellular cancer derived from HBV infection.

It is also the aim of this invention to use the HBcAg antigen that has mRNA in a proportion of more than 45% of the total RNA of this antigen and the HBsAg antigen to increase the immune response against an additional antigen that is co-administered with the mixture of these antigens. In a realization of the invention, the HBsAg forming part of the antigen mixture has phosphatidylserine at a proportion of over 5% of the total amount of phospholipids of this antigen.

The mixture of antigens referred to above can be used in the potentiation of the immune response against CHB (in a therapeutic scenario) or under strategies for preventive vaccination where the vaccine is multivalent. This is so because in addition to the increase in immunogenicity of the HBsAg and HBcAg antigens modified in a particular form, it was possible to verify that they are able to induce a potentiating immunogenicity effect of the heterologous antigens. The results of the experimental evaluations demonstrate that these antigens found in multivalent formulations can be useful for prophylactic or therapeutic use.

Although in relation to the formulations in the current invention the use of adjuvants, stabilizers or other additives can be avoided, this does not limit the introduction of additives, excipients, diluents that do not reduce the immunogenicity of the formulation or of the resulting final product, or the anti-viral efficacy of the formulation administered.

With the pharmaceutical composition and with the method for the immunoprophylaxis or the immunotherapy of the invention, a sustained antiviral response is achieved, and the number of patients reaching seroconversion of the HBsAg to anti-HBsAg is increased, compared to the composition and methods known in this technical field.

DETAILED ACCOUNT OF THE MODES OF REALIZATION/EXAMPLES OF REALIZATION

Example 1. Obtaining the HBcAG Protein with Different Proportions of the RNA Variants The HBcAg was obtained from a strain of *E. coli* that was genetically transformed with a plasmid that carried the gene codifying for this antigen [Aguilar J C, et al. Immunol Cell Biol (2004) 82:539-46].

On characterizing the particles of HBcAg, from the fermentative process made during different periods of time, it was observed that there was an increase in the proportion of mRNA incorporated in the preparations of HBcAg produced with longer fermentation periods. After 20 hours of fermentation, the levels of mRNA in the antigen increased more than 20%, compared to the HBcAg obtained in processes of up to 14 hours, as observed in Table 1. No significant changes were detected in the total amount of RNA in the particle, since no significant differences were found in the levels of total RNA, or in the ratio of RNA content/protein content. However, there was a significant increase in the level of mRNA when compared to other variants, specifically the ribosomal RNA (rRNA), which showed a reduction in its presence with the increase of the mRNA. No other relevant changes were found in the minor components associated to HBcAg or in specific contaminants, on carrying out trials by mass spectrometry or other chemical and physical studies.

TABLE 1

Variation of the percentage in relation to the main types of RNA in the HBcAg according to the duration of the fermentation process

| Variant | tRNA (%) | rRNA (%) | mRNA (%) |
|---|---|---|---|
| 1 (10 hr) | 0.1 | 76.3 | 23.6 |
| 2 (12 hr) | 0.1 | 60.0 | 39.9 |
| 3 (14 hr) | 0.09 | 54.9 | 45.0 |
| 4 (16 hr) | 0.09 | 40.0 | 59.1(*) |
| 5 (18 hr) | 0.1 | 34.5 | 65.5(*) |
| 6 (20 hr) | 0.1 | 32.8 | 67.1(*) |

The results represent the average values of the five determinations. In the column titled "Variant" the duration time of the fermentation is indicated in parenthesis. tRNA: transference RNA, rRNA: ribosomal RNA and mRNA: messenger RNA. (*): Significant differences (p<0.05).

Evaluation in Balb/c Mice of the Immunogenicity of the Variants of HBcAg with Different Percentages of mRNA Incorporated After obtaining the different variants of HBcAg with different percentages of the mRNA incorporated inside the particle (Table 1), the immunological evaluations of these preparations was carried out in Balb/c mice. For this study we used female mice of between 8 and 12 weeks of age, receiving two immunizations on days 0 and 15, through the SC route, with a dose of 1 µg of HBcAg in phosphate buffered saline (PBS), administrating a final volume of 100 µL. The detailed description of the schedule is shown in Table 2.

TABLE 2

Design of the immunization schedule to evaluate the influence of the percentage of mRNA incorporated in the particle of HBcAg in the immunogenicity of this antigen.

| Group | Treatment | No. of animals |
|---|---|---|
| 1 | 1 ug HBcAg (23% mRNA) | 10 |
| 2 | 1 ug HBcAg (39% mRNA) | 10 |
| 3 | 1 ug HBcAg (45% mRNA) | 10 |
| 4 | 1 ug HBcAg (60% mRNA) | 10 |
| 5 | 1 ug HBcAg (65% mRNA) | 10 |
| 6 | 1 ug HBcAg (67% mRNA) | 10 |
| 7 | PBS 1X | 10 |

Blood extractions for the evaluation of the specific antibody response generated by immunization were performed 10 days after the second dose. The measurement of antibody anti-HBcAg response was carried out using the ELISA technique.

Figure 1:
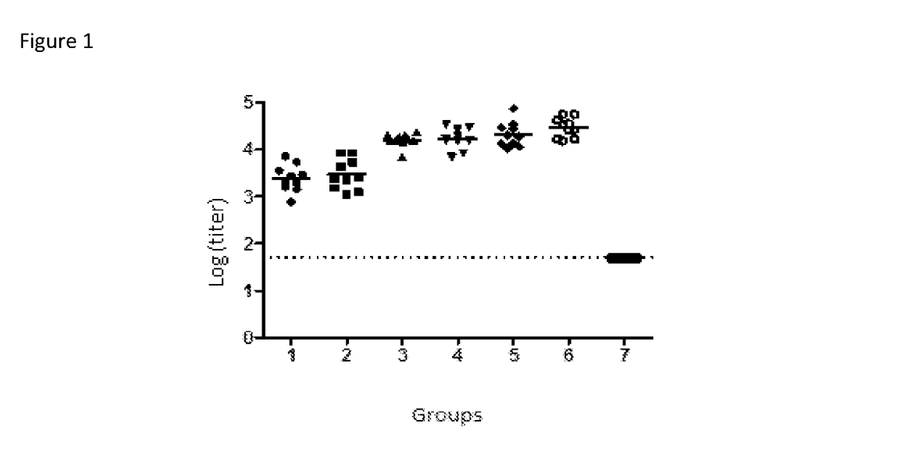
FIG. 1. Response of IgG anti-HBcAg antibodies after administering two doses.

As observed in FIG. 1, showing the IgG antibody titers anti-HBcAg obtained in each study group, the IgG anti-HBcAg response generated was significantly higher for the groups receiving the HBcAg with mRNA incorporated at above 45% (groups from 3 to 6 of Table 2). Among groups 3, 4, 5 and 6, no significant differences were detected, although there is a slight trend towards an increase of the IgG response associated to the increase in the percentage of mRNA incorporated. The results indicate that the increase in the proportion of mRNA incorporated inside the HBcAg particle at levels above 45% with respect to the total RNA incorporated confers a greater humoral immunogenicity to this protein. The preliminary analyses of the pattern of IgG subclases, suggest a similar performance at the level of the cellular type immune response.

Example 2. Obtaining the Virus Like Particles (VLP) of HBsAg with Different Proportions of Phosphatidylserine The recombinant HBsAg was obtained from a strain of genetically transformed *P. pastoris* using the gene that codifies this antigen [European Patent No. EP 480525]. It is known that the HBsAg expressed in this yeast species contains phosphatidylserine within its structural lipids [Lobaina Y, et al. Biotecnología Aplicada (2008), 25:325-331]. However, up until this invention, the influence of the presence of this lipid in the immunogenicity of this antigen had not been studied.

In order to study how the proportion of phosphatidylserine affects the immunogenicity of the HBsAg, we obtained the preparations of this VLP under different fermentation conditions. During the culture in recombinant yeast fermenters, we increased the concentration of $Mg^{(2+)}$ in the culture medium, to percentages of between 1.0 and 2.0%, which led to the increase of this phospholipid associated to the VLP of HBsAg. This was detected by using thin layer chromatography during the characterization of the HBsAg obtained under the different growth conditions.

The phosphatidylserine is associated to the VLP of the HBsAg, of known lipid nature. The results shown in Table 3 represent the average values of the five different repetitions. The purification was similar for all preparations of HBsAg produced under different experimental conditions. As observed in the table, there was no detection of phosphatidylserine in the samples obtained when the fermentation was carried out with a culture medium that contained a concentration of $Mg^{(2+)}$ at less than 1.2%. The levels of phosphatidylserine found in the preparation obtained with culture media containing 2.0% $Mg^{(2+)}$ were significantly higher than those found in the preparation obtained with the culture medium containing 1.4% $Mg^{(2+)}$ (Variant C).

TABLE 3

Obtaining the variants of the HBsAg with growing amounts of phosphatidylserine

| Variant | $Mg^{(2+)}$ Concentration (%) | FS (%) |
|---|---|---|
| A | 1.0 | ND |
| B | 1.2 | ND |
| C | 1.4 | 2.5 ± 0.3 |
| D | 1.6 | 5.0 ± 0.4 (*) |
| E | 1.8 | 6.1 ± 0.4 (*) |
| F | 2.0 | 7.7 ± 0.5 (**) |

ND: Not detected.
$Mg^{(2+)}$ (%): concentration of the Mg ion (in percentage) found in the saline additives of the culture medium.
FS (%): percentage of phosphatidylserine within the total phospholipids, determined after the extraction of the purified HBsAg.
(*): Significant differences ($p < 0.05$), (**) Highly significant differences ($p < 0.01$).

The preparations of the HBsAg represented in Table 3 were identical in their protein composition, according to the characterization made to study their primary, secondary and tertiary structure, comparable to the original variant. It is important to point out that the lipid concentration/protein concentration ratio did not change for any of the variants in the study. The same finding was obtained with the proportion of total phospholipids vs. the total protein content. No other significant changes took place during the analyses of impurities of the HBsAg or of other minor compounds, as a result of the analysis of their composition using mass spectrometry.

Example 3. Immunological Evaluation of the HBsAg Preparations Showing Different Percentages of Phosphatidylserine With the aim of evaluating if the presence of the phosphatidylserine affects the immune response against HBsAg, we carried out an immunogenicity study in transgenic mice that expressed the HBsAg in the serum [Castro F O, et al. Interferón y Biotecnología (1989) 6:251-257; Pérez A, et al. Acta Biotechnol (1993) 13: 373-383]. Seven groups of six mice each were used. These were female mice of 8-12 weeks of age that were immunized by the intranasal route (IN). The first six groups of the study received 5 μg each of the different variants of the HBsAg described in Table 3 with the Freund adjuvant. The seventh group was used as the control group and received PBS 1×. All treatment groups received 10 doses of the immunogen, which was administered every 14 days. The blood extractions were carried out before the initial immunization and 10 days after each dose, as of the third dose. In Table 4 the levels of HBsAg in the blood of transgenic mice are shown, as well as the levels of cytokines (IFN gamma (IFN-γ), tumoral necrosis factor (TNF-α), and IL-2 induced in supernatants of splenocyte cultures, isolated after administrating the 10 dosages. The evaluations were made using the ELISA technique.

After the administration of 5 μg of HBsAg, by the IN route in 10 successive immunizations, the concentration of HBsAg in the blood of transgenic mice for HBsAg was significantly reduced, when the level of the phosphatidylserine in this HBsAg was of 5% or more (variants D, E and F in Table 3, Example 2). In the same way, the variants of HBsAg of 5% or more phosphatidylserine induced significantly superior levels of IFN-γ, TNF-α and IL-2, compared to variants with low levels (variant C) or those where phosphatidylserine was undetectable, suggesting a dose-dependent effect. This is observed in Table 4.

When compared to the HBsAg that does not contain any phosphatidylserine, there was a significant increase of the Th1 cytokines and a higher elimination capacity of the circulating HBsAg was found after the immunization of transgenic HBsAg mice with variants of HBsAg containing levels of more than 5% phosphatidylserine (Table 4, variants D to F). The cytokine levels that are found for variants D-F were significantly higher than those of conditions A-C. The D-F variants induced the strongest reductions in the concentration of HBsAg, as well as the most potent secretions of cytokines after the in vitro stimulation of spleen cells in immunized transgenic animals.

TABLE 4

Evaluation of the circulating HBsAg and the levels of cytokines after the immunization of transgenic mice with variants of HBsAg with different percentages of phosphatidylserine.

| Variant of HBsAg | % Reduction of the HBsAg Concentration | Secretion of the IFN-γ (pg/mL) | Secretion of TNF-α (pg/mL) | Secretion of IL-2 (pg/mL) |
|---|---|---|---|---|
| A | 20 ± 3 | 50 ± 7 | 37 ± 6 | 14 ± 6 |
| B | 23 ± 4 | 65 ± 12 | 45 ± 18 | 22 ± 4 |
| C | 26 ± 5 | 149 ± 15 | 200 ± 26 | 36 ± 7 |
| D | 66 ± 5 (*) | 250 ± 20 (*) | 570 ± 30 (*) | 50 ± 5 (*) |
| E | 70 ± 6 (*) | 300 ± 27 (*) | 660 ± 27 (*) | 77 ± 8 (*) |
| F | 90 ± 5 () | 359 ± 31 () | 750 ± 37 () | 90 ± 10 () |

A-F: Variants of HBsAg produced with growing levels of phosphatidylserine in their composition, shown in Table 3.
(*): Significant differences ($p < 0.05$), (**) Highly significant differences ($p < 0.01$).

As observed, there was a significant increase of Th1 cytokines and a greater elimination capacity of the circulating HBsAg, by the immunization of the mice that were transgenic to HBsAg with the variants of HBsAg having a higher content of phosphatidylserine, thereby demonstrating an increase of the immunogenicity of the antigen with the increase in the proportion of this lipid component within the lipids associated to the VLP formed by this antigen.

The insertion of the phosphatidylserine in the particles of HBsAg had been previously reported in the state of the art. However, the way that the proportion of this component affects the immunogenicity of these particles had not been studied. Although in 2008 Lobaina et al. had speculated on the role of the phosphatidylserine in the higher HBsAg produced in *P. pastoris* [Lobaina Y, et al. Biotecnología Aplicada (2008), 25:325-331], in this same report it was demonstrated that two vaccines based on HBsAg produced in the same host differed in terms of immunogenicity, although the levels of the phosphatidylserine were presumably the same, because of the yeast species producing it.

Example 4. Demonstration of the Increase of Immunogenicity in Patients with CHB of Variants of HBcAg Having a Higher Proportion of Encapsulated mRNA In Example 1 it was proven in mice that there was an increase in the immunogenicity of the HBcAg with the increase in the proportion of the mRNA within the total amount of encapsulated RNA. Taking these results into account, the immunological behavior and the antiviral in vivo response of the formulations including both HBcAg and HBsAg, with modifications in their mRNA and phosphatidylserine, respectively, were characterized.

For this, a phase II randomized and double blind clinical trial was carried out in chronic hepatitis B patients. The patients selected had high viral loads of above 10 000 copies/mL and the HBeAg was positive at the start of the study. The patients were distributed in 6 groups, of 15 patients each, to which the treatments described in Table 5 were administered. A total of 10 dosages were given, which were divided into two cycles of 5 doses each, with an interval of one month between them. The first 5 doses were administered by the IN route alone, and the other 5 were administered IN/SC at the same time. In both administration cycles the doses were given at 14 day intervals.

TABLE 5

Treatment groups in the phase II clinical trial where the evaluation of the HBcAg and HBsAg antigens with modifications in the content of the mRNA and the phosphatidylserine, respectively, were carried out

| Groups | Treatment |
|---|---|
| 1 | 50 μg mHBsAg + 50 μg mHBcAg |
| 2 | 100 μg mHBsAg + 100 μg mHBcAg |
| 3 | 1000 μg mHBsAg + 1000 μg mHBcAg |
| 4 | 50 μg HBsAg + 50 μg HBcAg |
| 5 | 100 μg HBsAg + 100 μg HBcAg |
| 6 | 1000 μg HBsAg + 1000 μg HBcAg | mHBcAg: HBcAg containing mRNA at a proportion of 50% of the total RNA of this antigen;
mHBsAg: HBsAg containing 7% phosphatidylserine within the lipid components of the VLP.

Surprisingly, significantly higher levels of seroconversion to HBeAg and HBsAg were found in the group of patients treated with the formulation containing both modified antigens (that is, the formulation that contained HBsAg with levels of phosphatidylserine of over 5%, and HBcAg with mRNA above 45%), when compared to the groups of patients treated with formulations without these characteristics (see Table 6). This shows the relevance of these modifications in the increase of the quality of the anti-viral response generated in the patients.

In human beings, the antigens were evaluated in the range of concentrations from 50 μg per antigen per dose, up to 1 000 μg per antigen per dose, with evidence of anti-viral response, in terms of seroconversion to HBsAg and HBeAg, virological control and sustained virological response of under 10 000 copies of DNA of the HBV per mL, at more than 1 year after the end of the treatment.

TABLE 6

Frequency of patients with seroconversion to HBeAg and to HBsAg at one year after the end of the treatment in the phase II clinical trial with HBcAg and HBsAg having modifications in their mRNA and phosphatidylserine content respectively.

| Treatment Groups | Seroconversion to HBeAg | Seroconversion to HBsAg |
|---|---|---|
| 1 | 6/15 | 2/15 |
| 2 | 7/15 | 3/15 |
| 3 | 12/15 | 6/15 |
| 4 | 3/15 | 0/15 |
| 5 | 3/15 | 0/15 |
| 6 | 4/15 | 0/15 |

Similar results were also found in the model of mice that were transgenic to HBsAg, where a trial was carried out to evaluate treatment groups that are similar to those described in Table 5, and a greater decrease of the circulating HBsAg was obtained, as well as higher anti-HBsAg antibody titers, and with an earlier appearance, for the groups receiving the formulations that contained the antigens with the modifications described above.

Interestingly, the formulations containing the variants of modified HBcAg and HBsAg developed more potent Th1 immunogenicity in mice transgenic to HBV and in patients, compared to the response obtained with the formulations containing the unmodified antigens, or the formulations that contained only one of these modified antigens.

Example 5. Adjuvant Effect of the HBcAg and HBsAg Antigens Having Modifications in their mRNA and Phosphatidylserine Content Respectively in Multivalent Formulations Adjuvant capacity was compared in this study, i.e., the increase of the immune response toward antigens that are co-administered, within a mixture of recombinant HBcAg and HBcAg proteins with modifications in their mRNA and phosphatidylserine content, respectively, with the mixture of unmodified HBcAg and HBsAg, through the parenteral and mucosal routes. For this purpose, the recombinant chimeric protein CR3 was selected; this is the multiepitopic antigen of HIV-1 [Iglesias E et al. J Biochem Mol Biol & Biophys (2001) 1:109-122]. Eight groups of eight female Balb/c ($H-2^d$) mice of 6-8 weeks of age were inoculated with: 1) PBS (Placebo) through SC immunization (which will hitherto be referred to as Placebo (SC); 2) Sodium acetate buffer (NaAc), pH=5.2, through IN immunization (Placebo (IN)); 3) the mixture of HBcAg (C) and HBsAg (S) through the SC route (C+S (SC)); 4) the mixture of HBcAg that contains mRNA in a proportion of 50% of the total RNA of this antigen (mC) and HBsAg that contains 7% of phosphatidylserine within its lipid components (mS) through the SC route (mC+mS (SC)); 5) C+S through the IN route (C+S (IN)); 6) mC+mS through the IN route (mC+mS (IN)); 7) mixture of CR3 with HBcAg (C) and HBsAg (S) through the SC route (CR3+C+S (SC)); 8) CR3+mC+mS (SC); 9) CR3+C+S (IN) and 10) CR3+mC+mS (IN). The dose used was of 5 µg of each antigen by each route; and the immunogens were administered on days 0, 7 and 21 of the immunization schedule. For the SC immunizations, the proteins were dissolved in PBS and adsorbed in 1.4 mg/mL of aluminum hydroxide (Superfos Biosector A/S, Vedbaek, Denmark). For the IN route, the proteins were dissolved in NaAc, pH=5.2. The animals were anaesthetized by the intra-peritoneal (IP) administration of 30 µL of ketamine (10 mg/mL), located in a supine position, and the immunogens were slowly dispensed in 50 µL (25 µL/per nostril) with a pipette tip. Ten days after the immunizations, the sera of all animals were collected and five animals were sacrificed (in a random manner) at the end of the study, to obtain their spleen for the studies of cellular immune response.

The response of IgG in the serum was evaluated through an indirect ELISA where the plates were coated with the CR3 protein. The methodology for the quantification of the secretion of IFN-γ in the supernatants of the cultures stimulated with CR3 have been previously informed [Garcia Diaz D et al. Immunol Lett (2013) 149:77-84].

The Gaussian distribution was evaluated for the statistical analysis of the data with the Kolmogorov-Smirnov test and the equality of variances with the Bartlett test. The samples with normal distribution (or those in which the Gaussian distribution is inferred) and with equal variance were compared with parametric tests; otherwise, the alternative non-parametric test was used. All titers of IgG were transformed to log 10, in order to achieve a normal distribution of the values. The sera of the animals that did not reach seroconversion were assigned an arbitrary titer of 1:10, for statistical processing. A value of $p<0.05$ was considered statistically significant.

Figure 2:
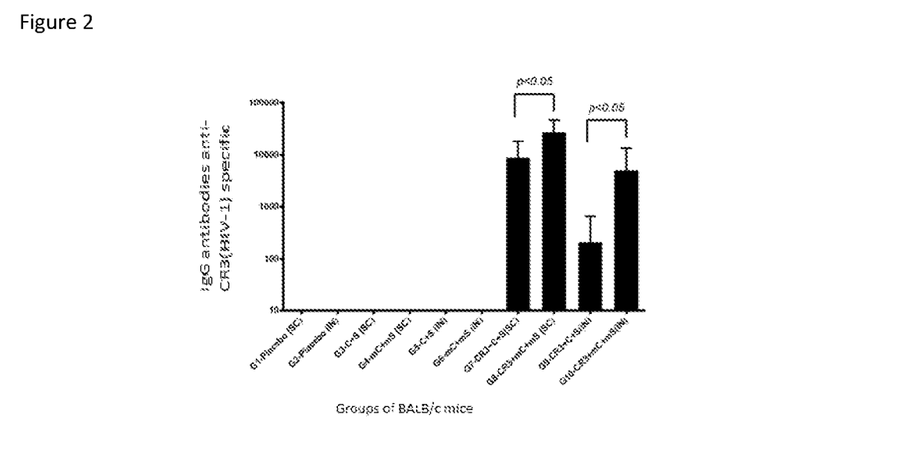
FIG. 2. AntibodiesIgG anti-CR3.

The results of the IgG anti-CR3 antibody determination (HIV-1), observed in FIG. 2, showed a higher response ($p<0.05$) after administrations through the SC and IN routes in the groups of animals immunized with the mixture of CR3+mC+mS (groups 8 and 10) vs CR3+C+S (groups 7 and 9), respectively. Consistent with the previous results, a greater secretion of IFN-γ was also observed in the supernatants of the cultures from mice of the same groups, as observed in Table 7. For this analysis, ten days after the last immunization (day 31), splenocytes from five mice per group were cultivated. Splenocyte suspensions of individual animals were prepared for the placebo group. They were stimulated ex vivo with 2.5 µg/mL of the CR3 protein for five days. In the supernatant liquids, the CR3-specific IFN-γ was quantified with a sandwich type ELISA. The detection limit was 0.80 ng/mL.

TABLE 7

Secretion of IFN-γ measured in the supernatant liquids of the cultures.

| Group | Inoculum | Replicate (mouse) | IFN-γ (ng/mL) |
|---|---|---|---|
| 1 | Placebo (SC) | Pool | <0.80 |
| 2 | Placebo (IN) | Pool | <0.80 |
| 3 | C + S (SC) | 1 | <0.80 |
|   |   | 2 | <0.80 |
|   |   | 3 | <0.80 |
|   |   | 4 | <0.80 |
|   |   | 5 | <0.80 |
| 4 | mC + mS (SC) | 1 | <0.80 |
|   |   | 2 | <0.80 |
|   |   | 3 | <0.80 |
|   |   | 4 | <0.80 |
|   |   | 5 | <0.80 |
| 5 | C + S (IN) | 1 | <0.80 |
|   |   | 2 | <0.80 |
|   |   | 3 | <0.80 |
|   |   | 4 | <0.80 |
|   |   | 5 | <0.80 |
| 6 | mC + mS (IN) | 1 | <0.80 |
|   |   | 2 | <0.80 |
|   |   | 3 | <0.80 |
|   |   | 4 | <0.80 |
|   |   | 5 | <0.80 |
| 7 | CR3 + C + S(SC) | 1 | 6.35 |
|   |   | 2 | 7.86 |
|   |   | 3 | 3.32 |
|   |   | 4 | 4.45 |
|   |   | 5 | 3.54 |
| 8 | CR3 + mC + mS (SC) | 1 | 10.35 |
|   |   | 2 | 9.86 |
|   |   | 3 | 8.62 |
|   |   | 4 | 9.05 |
|   |   | 5 | 11.24 |
| 9 | CR3 + C + S(IN) | 1 | <0.80 |
|   |   | 2 | 2.03 |
|   |   | 3 | 1.68 |
|   |   | 4 | 0.97 |
|   |   | 5 | 2.25 |
| 10 | CR3 + mC + mS (IN) | 1 | 4.55 |
|   |   | 2 | 5.36 |
|   |   | 3 | 3.87 |
|   |   | 4 | 2.54 |
|   |   | 5 | 3.98 |

Figure 3:
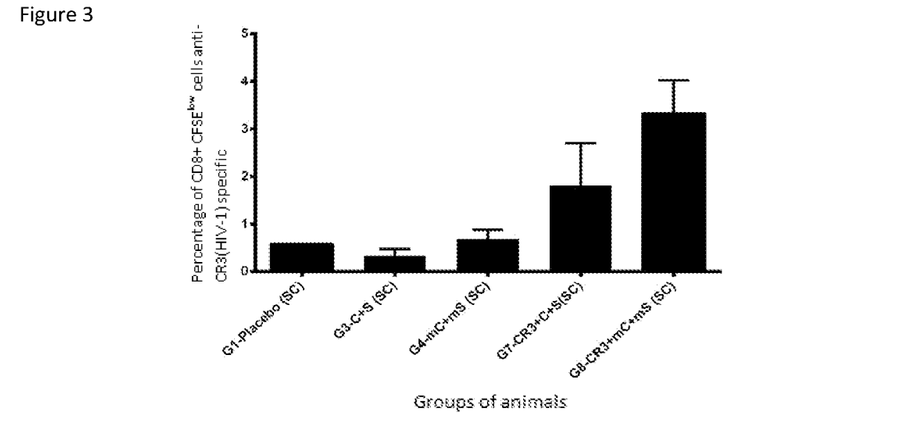
FIG. 3. Proliferative response of T cells CD8+CR3 (HIV-1)-specific.

Finally, the frequency of the CD8+ cells that are specific for CR3 (HIV-1) were compared after the ex vivo stimulation in the groups immunized by the SC route. A higher frequency of CD8+ cells were obtained in the stimulated group in CR3+mC+mS (SC) vs CR3+C+S (SC) ($p<0.05$), which is observed in FIG. 3.

These results, as a whole, show that the mixture of HBcAg having mRNA above 45% (mC) and of HBsAg with levels of phosphatidylserine above 5% (mS) have a higher Th1 adjuvant effect, by the parenteral and mucosal routes. Particularly, for the vaccination against HIV, this result is of great importance, because the antiviral Th1 response has been related to the protection against the infection and progression to AIDS.

Although it was not the objective of this experiment to measure the humoral response against the HBsAg and HBcAg antigens (abbreviated in this example as C and S), we observed responses of IgG anti-HBcAg and anti-HBsAg that were higher and statistically significant, in the groups of mice immunized with the mixture of the modified HBsAg and HBcAg antigens (mC+mS), when compared to the mixture of unmodified HBsAg and HBcAg (C+S, data not shown). This confirmed the above results.

Example 6. Passive Immunization Through the Adoptive Transfer of Cells from Balb/c Mice Immunized with Formulations of the HBcAg and HBsAg with Modifications in their mRNA Content and of Phosphatidylserine, Respectively, to Transgenic Balb/c Mice Expressing the HBsAg In this invention we wished to potentiate the immune response anti-HBsAg and anti-HBcAg in donors through the active immunization of individuals with a formulation containing the antigens of HBsAg and HBcAg, which include modifications in their content of phosphatidylserine and of mRNA, respectively and also, the cells to be transferred would be activated in vitro before the transfer, so that the response against these antigens would be maximum when the cells are inoculated into the receptor organism. Hence, a type of response that is inexistent in persons, would be obtained in an artificial manner, making it possible to increase the margin of donors to persons with similar haplotypes, regardless of whether they have been infected or not by HBV.

In the current example we evaluated, through the adoptive transfer of cells, the effect of the immune response generated by vaccination with a formulation composed of the HBsAg and HBcAg antigens with modifications in their content of phosphatidylserine and of mRNA, respectively, which is applied by the IN/parenteral routes, in the context of a transgenic mouse that expresses the HBsAg, a model of the persistent infection of the HBV. One of the objectives of the study was the evaluation of the effect of the transferred immune response on the concentration of HBsAg (antigenemia) in the serum of the transgenic mouse. Furthermore, we compared the effect of the response induced by the combination of IN/parenteral routes for the administration of the formulation of the HBsAg and HBcAg antigens in relation to the effect generated by the transfer of cells stimulated only with HBsAg in vivo and in vitro. Additionally, the kinetics of the antibody response anti-HBsAg transferred in the context of the transgenic mouse for this antigen, was studied. We used Balb/c mice and mice that were HBsAg (+) transgenic (with a genetic background of Balb/c, obtained at the CIGB).

Generation of Immunity Anti-HBsAg in Balb/c Mice

An immunization schedule was carried out in Balb/c female mice of 8 to 12 weeks of age. The mice were immunized with a vaccine preparation containing the modified antigens HBsAg (with a content of phosphatidylserine of more than 5%) and HBcAg (with a content of mRNA of more than 45%), simultaneously by the IN and parenteral routes. Within the parenteral route, we tested the IM, SC and ID routes. The dosage (in volume of 100 μL) was administered on days 0 and 14, and a booster shot was administered on day 100, before the transfer. The blood extractions were made at the retro-orbital plexus on days 2, 10 and 25. Table 8 shows the design of the immunization schedule, including the treatment received by each group.

TABLE 8

Immunization schedule in non-transgenic Balb/c mice

| Group | Treatment | Route | Number of animals |
|---|---|---|---|
| 1 | mHBsAg + mHBcAg + alúmina/ mHBsAg + mHBcAg | IM/IN | 13 |
| 2 | mHBsAg + mHBcAg + alúmina/ mHBsAg + mHBcAg | SC/IN | 13 |
| 3 | mHBsAg + mHBcAg + alúmina/ mHBsAg + mHBcAg | ID/IN | 13 |
| 4 | mHBsAg + mHBcAg/ mHBsAg + mHBcAg | IM/IN | 13 |
| 5 | mHBsAg + mHBcAg/ mHBsAg + mHBcAg | SC/IN | 13 |
| 6 | mHBsAg + mHBcAg/ mHBsAg + mHBcAg | ID/IN | 13 |
| 7 | alúmina/ PBS | IM/IN | 9 | mHBcAg: HBcAg containing mRNA at a proportion of 50% of the total RNA of this antigen;
mHBsAg: HBsAg containing 7% of phosphatidylserine within the lipid components of the VLP.

The evaluation of the immune humoral response generated by these treatments was carried out by measuring the IgG response and the subclasses of IgG anti-HBsAg, after each inoculation, using the ELISA technique. In order to evaluate the cellular immune response, at 10 days after the first administration, we carried out an ELISPOT type trial to measure the secretion of specific IFN-γ against the HBsAg by the CD8+ lymphocytes from the spleen. The results of these evaluations indicate that Group 5 generates the greatest cellular response and a humoral response that does not differ from the rest of the groups studied. Based on this, we selected two animals from this group as splenocyte donors for adoptive transfer. The selection of the immunogen was carried out at a proportion of 1:1 (HBsAg:HBcAg)

Obtaining Immune-Splenocytes

Fifteen days after receiving the booster shot, the two mice from Group 5, and three mice from Group 7 (placebo) were sacrificed and their spleen was extracted. The spleens from Group 5 and those of Group 7, respectively, were grouped. The spleens were processed until the splenocytes were obtained. They were separated into aliquots of $30\times10^6$ cells in 100 μL of PBS 1×, for their transfer to the receptor mice.

Adoptive Transfer of Immunity

Transgenic mice expressing the HBsAg that were used as receptors were of between 16-20 weeks of age and from both sexes. They were assigned to the different treatment groups as shown in Table 9. Before the transfer of splenocytes, a partial blood extraction was carried out to check the levels of HBsAg in the serum. Afterwards, we inoculated (through the IP route) 30×10⁶ splenocytes in a volume of 100 μL of PBS 1×. The blood extractions to evaluate the effect of the adoptive transfer of immunity were made through the retro-orbital plexus, each week for 5 weeks. On week 8 post-transfer, the animals were bled and sacrificed.

TABLE 9

Design of the experiment of adoptive transfer of immunity

| Group | Treatment | Number of animals |
|---|---|---|
| 1 | Transfer of splenocytes* from Balb/c mice with a response to HBsAg and HBcAg | 3 |
| 2 | Transfer of splenocytes from Balb/c placebo mice | 3 |
| 3 | PBS 1x | 3 |

Quantification of the HBsAg in the Serum of Mice Transgenic for HBsAg

The levels of HBsAg in the serum were determined by ELISA. The plates were coated with the monoclonal antibody anti-HBsAg called Hep4 (produced by CIGB). All mice receiving cells with a previous immunity to HBsAg showed, from the evaluation on the week after the transfer, a marked decrease of the HBsAg in the serum, with significant differences between time zero and the $2^{nd}$ and $3^{rd}$ weeks ($p<0.05$). As of the fourth week (day 35) we observed that the concentrations of HBsAg in the serum started increasing, thus indicating that the control of the anti-genemia by the transferred immunity is decreasing. As of this point, and up to week 8 (day 63), there are no differences in the anti-genemia, with that reported for time zero of the trial.

In the case of the mice receiving the splenocyte transfer with specific immunity against HBsAg, we detected marked decreases of the HBsAg in the serum, which were more notable between days 7 and 28. However, for the mice that received the placebo splenocyte transfer, or the PBS, although there are changes in the concentration of the HBsAg in the serum, it never reached a significant difference with time zero, and values below 5 μg/ml were never detected.

These results indicate that it is possible, through the adoptive transfer of immunity, mediated by cells, to effectively decrease the levels of HBsAg circulating in the serum of these transgenic animals of this protein. The control established on the anti-genemia, by the immune response transferred in this case, was effective, and lasted about 3 weeks after a single cell transfer.

IgG Anti-HBsAg Response in the Serum

A specific IgG antibody response against HBsAg was detected for all mice receiving the transfer of splenocytes with prior immunity for this antigen. This agrees with the anti-genemia results obtained. In the case of the animals with an anti-HBsAg response, the titers detected were high (Titer>$10^4$) and started to decrease as of the third week, which may be related to the increase of the anti-genemia that is observed for these animals at about the $4^{th}$ week (day 35). The groups receiving the transfer of placebo cells or PBS do not show specific antibodies.

The invention claimed is:

1. A method for immunoprophylaxis or immunotherapy against infection of hepatitis B virus (HBV), said method comprising administering to an individual in need thereof an effective amount of a pharmaceutical composition comprising i) core antigen of the hepatitis B virus (HBcAg) that includes messenger ribonucleic acid (mRNA) for the HBcAg antigen at a proportion of more than 45% of total ribonucleic acid (RNA) in the HBcAg antigen, and ii) surface antigen (HBsAg) of the hepatitis B virus (HBV), wherein the HBsAg includes phosphatidylserine at a proportion of over 5% of the total amount of phospholipids in the HBsAg.

2. The method of claim 1 wherein the pharmaceutical composition is administered by the parenteral and mucosal routes.

3. The method of claim 1 wherein the individual receiving the immunotherapy is a patient with chronic hepatitis B (CHB).

4. The method of claim 3 wherein the immunotherapy of the CHB patients is used for the prevention of hepatocellular cancer derived from the HBV infection.

* * * * *